(12) United States Patent
Chiel et al.

(10) Patent No.: US 7,857,369 B2
(45) Date of Patent: Dec. 28, 2010

(54) BIOLOGICALLY INSPIRED GRIPPING DEVICE

(75) Inventors: Hillel Judah Chiel, University Heights, OH (US); Randall Dean Beer, South Enclid, OH (US); Elizabeth Victoria Mangan, Cleveland Heights, OH (US); Roger D. Quinn, Akron, OH (US); Gregory Patrick Sutton, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1397 days.

(21) Appl. No.: 11/172,526

(22) Filed: Jun. 30, 2005

(65) Prior Publication Data

US 2006/0004395 A1 Jan. 5, 2006

Related U.S. Application Data

(60) Provisional application No. 60/584,281, filed on Jun. 30, 2004.

(51) Int. Cl.
*B66C 1/42* (2006.01)
*A61B 17/22* (2006.01)

(52) U.S. Cl. .................. 294/86.4; 606/159; 604/101.01

(58) Field of Classification Search ................. 294/86.4; 604/95.03, 101.01; 606/159
See application file for complete search history.

(56) References Cited

U.S. PATENT DOCUMENTS

| | | | | |
|---|---|---|---|---|
| 2,855,934 A | * | 10/1958 | Daughaday, Jr. | 604/95.03 |
| 4,176,662 A | * | 12/1979 | Frazer | 600/114 |
| 4,407,275 A | * | 10/1983 | Schroeder | 600/38 |
| 4,447,227 A | * | 5/1984 | Kotsanis | 604/95.03 |
| 4,921,484 A | * | 5/1990 | Hillstead | 606/194 |
| 5,242,398 A | * | 9/1993 | Knoll et al. | 604/101.05 |
| 5,540,731 A | * | 7/1996 | Testerman | 607/42 |
| 5,749,883 A | * | 5/1998 | Halpern | 606/159 |
| 6,764,441 B2 | | 7/2004 | Chiel et al. | |
| 6,988,986 B2 | * | 1/2006 | Gross | 600/115 |

OTHER PUBLICATIONS

Causey, G., Guidelines for the design of robotic gripping systems. Assembly Automation, 2003. 23: p. 18-28.

Marcincin, J.N. and J. Smrcek, Biomechanical grippers: important elements of biomechanical robots. Industrial Robot, 1997. 24: p. 234-238

Arimoto, S., K. Tahara, M. Yamaguchi, P.T.A. Nguyen, and H.-Y. Han, Principles of superposition for controlling pinch motions by means of robot fingers with soft tips. Robotica, 2001. 19: p. 21-28.

Zajac, T.J. Robotic Gripper Sizing: The Science, Technology and Lore. http://www.grippers.com/size.htm, 2002.

Taylor, P., Presentation and gripping of flexible materials. Assembly Automation, 1995, 15: p. 33-35.

Brusca, R. and G. Brusca, Invertebrates. 1990 Sunderland, MA: Sinauer Associates, Inc., p. 728-738.

(Continued)

*Primary Examiner*—Paul T Chin
(74) *Attorney, Agent, or Firm*—Tarolli, Sundheim, Covell & Tummino LLP

(57) ABSTRACT

A flexible gripping device including a plurality of pneumatic actuator rings. A grasper element is disposed within the plurality of pneumatic actuator rings and adapted to move back and forth within the actuator rings.

14 Claims, 8 Drawing Sheets

OTHER PUBLICATIONS

Kandel, E., Behavioral Biology of Aplysia. 1979, San Francisco: W. H. Freeman and Co., p. 88-96.

Kupfermann, I., Feeding behavior in Aplysia: A simple system for the study of motivation. Behay. Bio., 1974. 10: p. 1-26.

Neustadter, D., R. Drushel, P. Crago, B. Adams, and H. Chiel, A kinematic model of swallowing in Aplysia californica based on radula/odontophore kinematics and in vivo magnetic resonance images. J exp Biol, 2002. 205: p. 3177-3206.

Colbrunn, R. W. Design and contrast of a robatic leg with braided pneumatic actuators. Department of Mechanical and Aerospace Engingeering, Case Western Reserve University, 2000. M.S. thesis, p. 1-37.

Bar-Cohen, Y., Actuation of biologically inspired intelligent robotics using artificial muscles. Industrial Robot, 2003. 30: p. 331-337.

Espenschield, K., R. Quinn, R. Beer, and H. Chiel, Biologically based distributed control and local reflexes improve rough terrain locomotion in a hexapod robot. Robotics and Autonomous Systems, 1996. 18: p. 59-64.

Mangan, E.V., D.A. Kingsley, R.D. Quinn, and H.J. Chiel, Development of a peristaltic endoscope. International Conference on Robotics and Automation 2002, 2002: p. 347-352.

Morton, D. and H.J. Chiel, In vivo buccal nerve activity that distinguishes ingestion from rejection can be used to predict behavioral transitions in Aplysia. J Comp Physiol A, 1993. 172: p. 17-32.

* cited by examiner

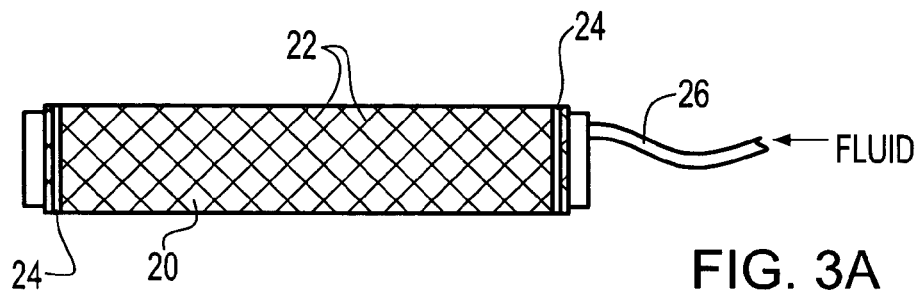
FIG. 3A
PRIOR ART
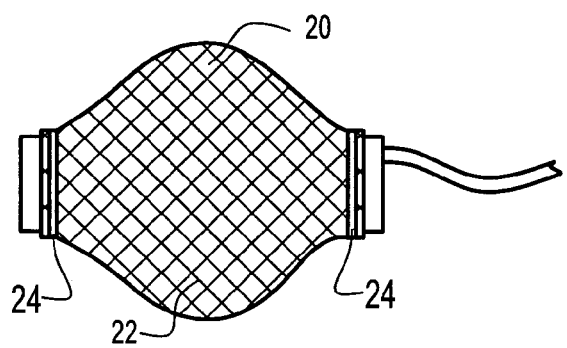
FIG. 3B
PRIOR ART
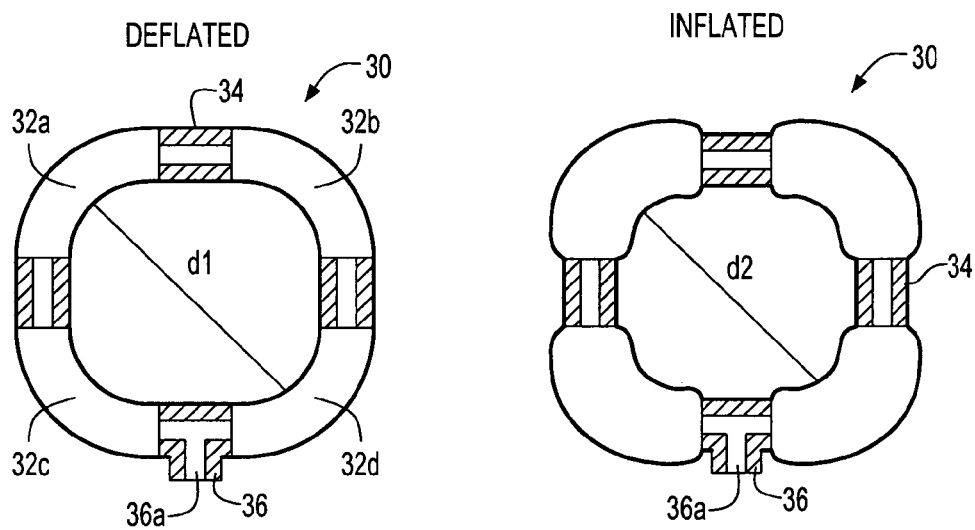
FIG. 4A   FIG. 4B

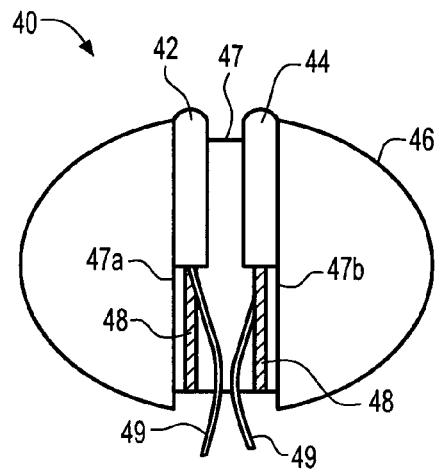 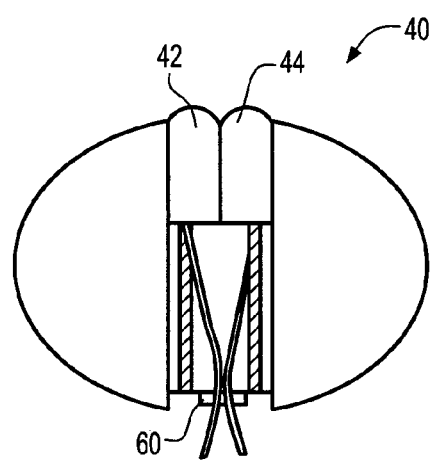
FIG. 5A　　　　　　　FIG. 5B
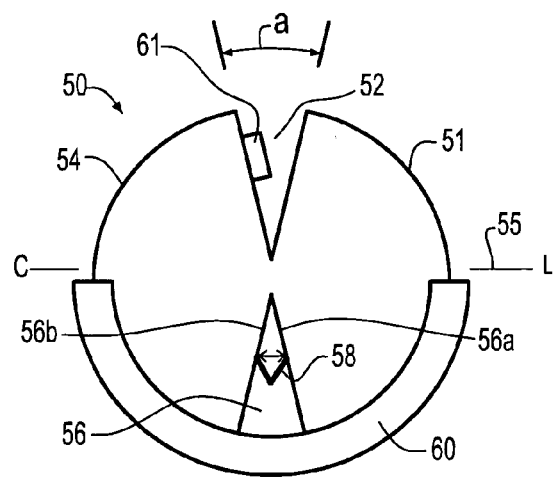 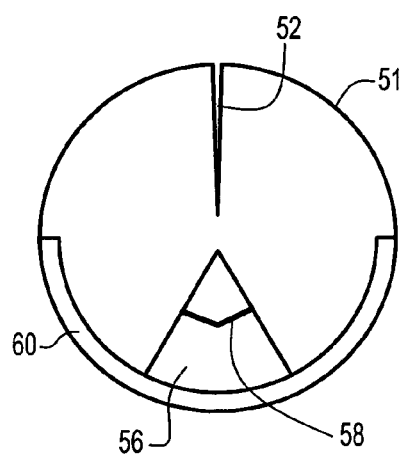
FIG. 6A　　　　　　　FIG. 6B

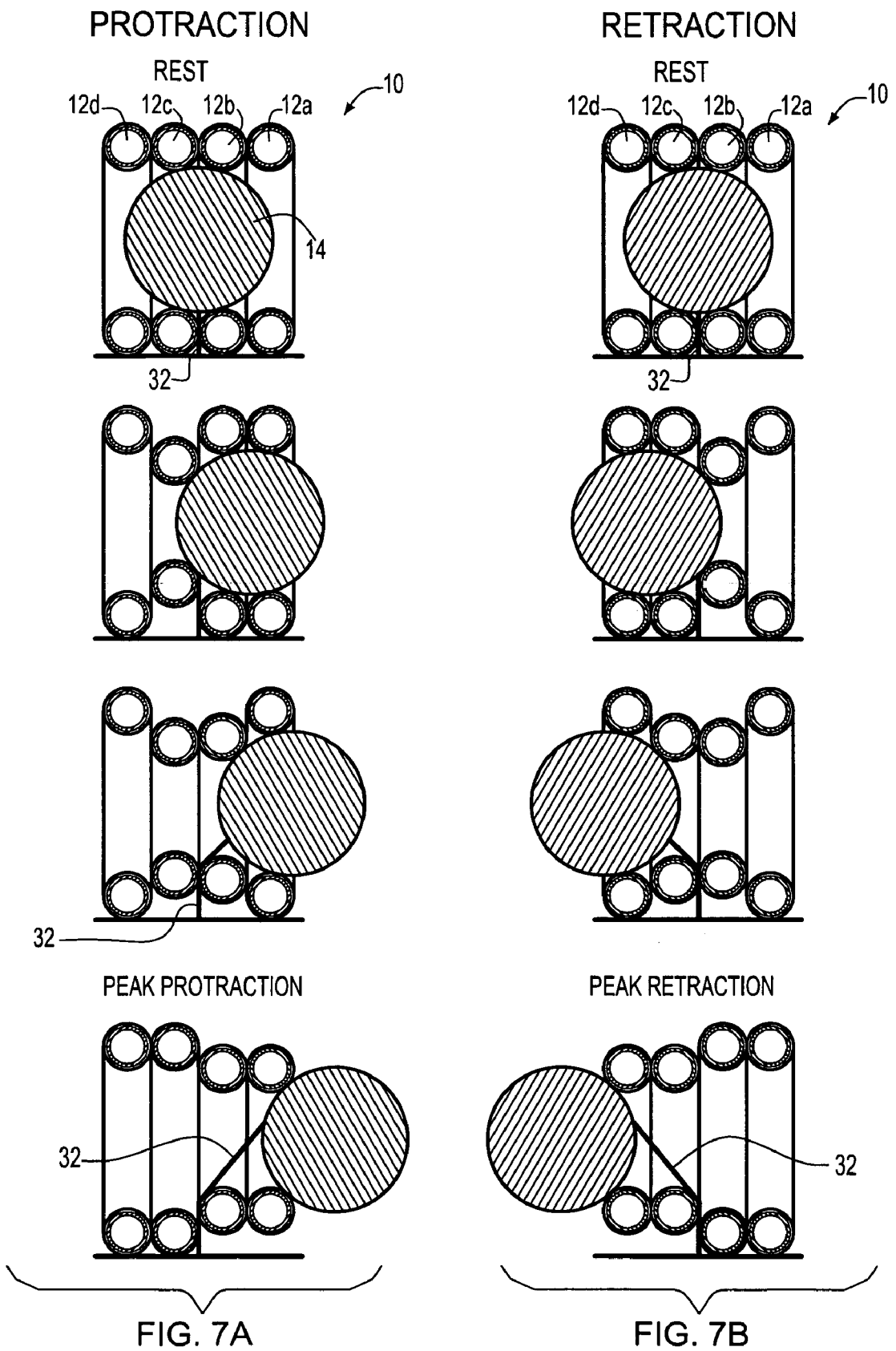

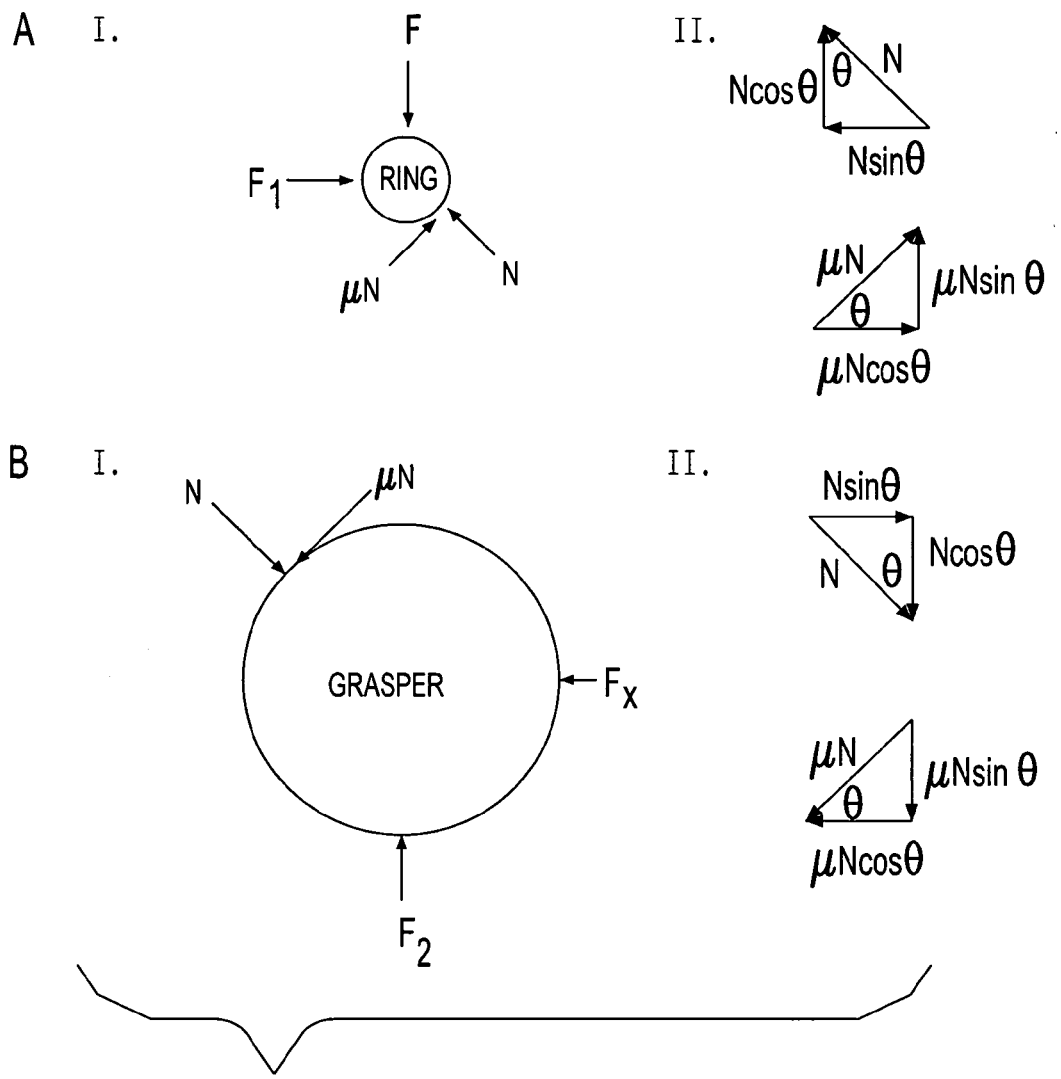
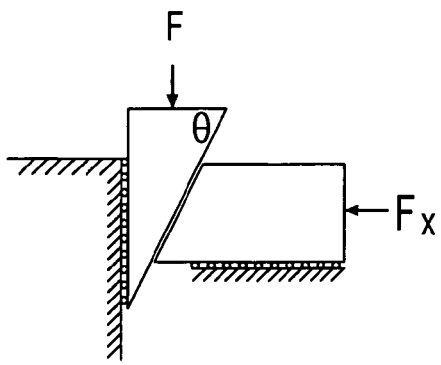
FIG. 10
FIG. 11

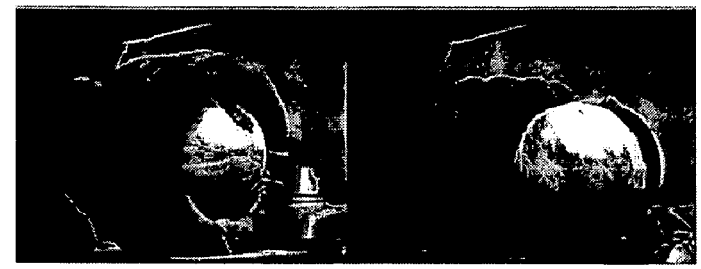
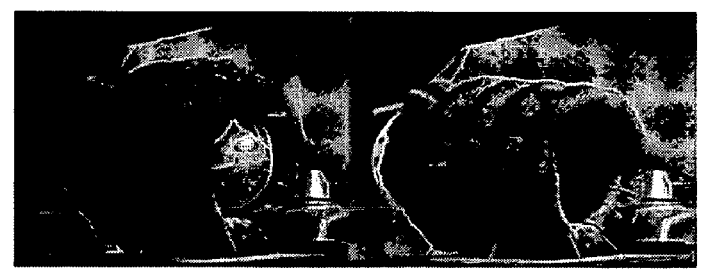
FIG. 12
FIG. 13

BIOLOGICALLY INSPIRED GRIPPING DEVICE

CROSS-REFERENCE TO RELATED APPLICATIONS

This application claims the benefit of U.S. Provisional Patent Application No. 60/584,281 filed on Jun. 30, 2004, which is incorporated herein by reference.

FEDERALLY SPONSORED RESEARCH

The contents of this application were developed under a Presidential Research Initiative Grant, NSF Grant IBN99-74394 and NSF grant IBN-0218386.

FIELD OF THE INVENTION

The present invention relates to control devices, and specifically to control of devices that are capable of gripping and manipulating materials.

BACKGROUND OF THE INVENTION

A major focus of robotic applications is the development and control of devices that are capable of gripping and manipulating materials. Basic grippers consist of two surfaces that can be brought together; more dextrous grippers use fingers, some of which can be individually controlled as disclosed in Causey, G., *Guidelines for the design of robotic gripping systems*. Assembly Automation, 2003, 23: p. 18-28; Marcincin, J. N. and J. Smrcek, *Biomechanical grippers: important elements of biomechanical robots*. Industrial Robot, 1997, 24: p. 234-238; and Arimoto, S., K. Tahara, M. Yamaguchi, P. Nguyen, and H.-Y. Han, *Principles of superposition for controlling pinch motions by means of robot fingers with soft tips*. Robotica, 2001, 19: p. 21-28. For rigid objects, grippers usually fall into two broad classes: friction grippers or encompassing grippers, as disclosed in the Causey article. If the gripper uses the friction between its surfaces and the object to grip it, the gripper requires about four times the force of an encompassing gripper, whose surfaces partially conform to those of the held object, as disclosed in Zajac, T. J., *Robotic Gripper Sizing: The Science, Technology and Lore*. http://www.grippers.com/size.htm, 2002.

Holding and manipulating soft or delicate materials is an area of intense research. A recent survey of devices that could grip materials such as fabrics, leathers, or food products found three major categories: pinching using friction (similar to the principles described above), intrusive grippers that insert pins into the material to lock it in place, and surface attraction grippers that make use of adhesives or vacuum, as disclosed in Taylor, P., *Presentation and gripping of flexible materials*, Assembly Automation, 1995. 15: p. 33-35. A difficulty with such prior art devices is that they may crush, deform, or in other ways change the properties of the object that has been gripped. Thus, it would be of great value and interest to develop grippers that could handle soft, pliable, fragile, slippery and irregular materials without inducing significant material deformation.

Biological organisms are frequently confronted with highly complex materials that they must manipulate to achieve their goals. For example, animals that feed on seaweed must be capable of harvesting large amounts of slippery, irregularly shaped material that is usually connected to a substrate by a holdfast. Many organisms have successfully solved these problems using a variety of different feeding mechanisms. One very successful group is the mollusks, which are capable of feeding on highly irregular materials using a feeding apparatus known as the radula (rasper) controlled by underlying musculature (the odontophore) and moved forward and backward by other muscles in order to contact food, and then convey food into the animal's body, as disclosed in Brusca, R. and G. Brusca, *Invertebrates*. 1990, Sunderland, Mass.: Sinauer Associates, Inc, p. 728-738.

The sea slug, *Aplysia californica*, uses a muscular structure called the buccal mass to grasp and ingest food. As shown in FIG. 1, the central grasper within the buccal mass consists of a thin, flexible surface covered with fine teeth (the radula), that is opened or closed by a set of muscles known as the odontophore. The structure is moved towards the jaws (protracted) using a thin, sheet like muscle (I2), and can be moved towards the esophagus using thick bands of muscle that form the jaws (I1/I3 jaw muscles), as disclosed in Kandel, E., *Behavioral Biology of Aplysia*, 1979, San Francisco: W. H. Freeman and Co., p. 88-96; Kupfermann, I., *Feeding behavior in Aplysia: A simple system for the study of motivation*; Behav. Biol., 1974, 10: p. 1-26; and Neustadter, D., R. Drushel, P. Crago, B. Adams, and H. Chiel, *A kinematic model of swallowing in Aplysia californica based on radula/odontophore kinematics and in vivo magnetic resonance images*. J exp Biol, 2002. 205: p. 3177-3206.

U.S. Pat. No. 6,764,441 and Mangan, E. V., D. A. Kingsley, R. D. Quinn, and H. J. Chiel, *Development of a peristaltic endoscope*. International Congress on Robotics and Automation 2002, 2002: p. 347-352, disclose a self-propelled device capable of peristaltic locomotion caused by a plurality of braided pneumatic actuators that surround a central flexible tube. This device demonstrates the use of braided pneumatic actuators for locomotion, whereas the device disclosed in this application demonstrates the use of these actuators for gripping and manipulating flexible and irregular materials. Moreover, the braided pneumatic actuators in that application are arranged in series, and thus are not used in the same form as disclosed in this application.

ASPECTS AND SUMMARY OF THE INVENTION

It is an aspect of the present invention to provide a device capable of gripping and manipulating materials.

It is a further aspect of the present invention to provide a biologically-inspired gripper device that can transfer pliable materials through a lumen.

It is a still further aspect of the present invention to provide a biologically-inspired gripper device that can surgically remove plaque from blood vessels and clean plumbing.

The present invention relates to a gripping device that is based on the feeding apparatus of a mollusk, known as the buccal mass. The device consists of four artificial muscle rings arranged in parallel. A grasper is placed in the middle of the rings. Sequential activation of the rings produces a peristaltic motion that moves the grasper back and forth within the rings. By activating the grasper appropriately, it can grab, ingest, and move soft and irregular material from one side of the lumen formed by the rings to the other side. Such a device would be useful in medical and plumbing applications, where the material to be removed is very compliant.

According to the present invention, a flexible gripping device comprises a plurality of pneumatic actuator sections each in the form of a pneumatic actuator ring; and a grasper element disposed within the plurality of pneumatic actuator rings and adapted to move back and forth within the actuator rings. The gripping device includes means for sequentially activating the plurality of actuator rings to produce a peristaltic motion that moves the grasper element back and forth within the actuator rings. The plurality of actuator rings can be disposed in parallel relation to each other and secured to each other to form a tubular device with a central interior or lumen through which the grasper element moves back and forth. The gripping device includes a means of connecting each of the actuator rings to an adjacent ring so that each of the actuator rings remain in contact with adjacent rings as any ring expands or contracts whereby each ring may expand in volume and occupy part of the central interior or lumen so as to exert force on the grasper element.

Also according to the present invention, structural means are provided to actuate the actuator rings to move the grasper element forwards or backwards relative to the central interior of the tubular device.

Further, according to the present invention, structural means are provided for returning the grasper element to an initial resting position in the central interior of the tubular device if the actuator rings are not actuated. The structural means for returning the grasper element can be an elastic band attached to the grasper element and to a substrate that constrain the grasper element to rotate and for pulling the grasper element back to the initial resting position.

Still further, according to an embodiment of the present invention, the grasper element comprises: a generally spherically shaped, elastomeric element; a first cleft shaped opening extending from a peripheral surface towards the interior of the elastomeric element; a second cleft shaped opening extending from an opposite side of the peripheral surface towards the interior of the elastomeric element; structural means, such as a spring, within the second cleft shaped opening to provide a passive closing force; and at least one pneumatic actuator disposed across the second cleft shaped opening and attached at opposite ends of the actuator to the peripheral surface for opening the second cleft shaped opening and simultaneously closing the first cleft shaped opening so as to enable them to grasp a material to be moved.

Also according to another embodiment of the present invention, the grasper element comprises: a generally ellipsoid shaped element with a groove having a flat bottom surface formed around the circumference of the ellipsoid shaped element; a pair of inflatable tubular actuators disposed in the groove and spaced from each other; structural means to inflate the tubular actuators so that they expand radially and press against each other to enable a material to be grasped and moved. The grasper element can include structural means for securing the pair of inflatable tubular actuators disposed in the groove. The groove in the grasper element can be disposed parallel to the minor axis of the generally ellipsoid shaped element.

According to the present invention, sensing means are provided for sensing physical properties encountered by the grasper element and control means to control the gripping device in response to the physical properties encountered by the grasper element. The control means of controlling the gripping device further includes means for responding to changes in physical properties encountered by the grasper element by altering the duration or intensity of protraction or retraction of the grasper element or opening or closing of the grasper element.

According to the present invention, a method of moving a material with a flexible gripping device comprises the steps of: providing a plurality of pneumatic actuator rings secured to each other to form a tubular device with a central interior; disposing a grasper element within the plurality of pneumatic actuator rings at an initial resting position; and sequentially activating the plurality of actuator rings to produce a peristaltic motion that moves the grasper element back and forth within the interior of the actuator rings.

Still further, according to the present invention, the method includes the step of returning the grasper element to the initial resting position in the central interior of the tubular device if the actuator rings are not actuated.

Also according to the present invention, the method includes the steps of: providing the grasper element with a pair of inflatable tubular actuators; and inflating the tubular actuators so that they expand radially and press against each other to enable a material to be grasped and moved.

Further, according to the present invention, the method includes the steps of sensing physical properties encountered by the grasper element; and controlling the gripping device in response to the physical properties encountered by the grasper element.

Still further, according to the present invention, the method includes the steps of changing the timing of opening and closing the grasper element relative to protraction and retraction of the plurality of actuator rings so that material can be transported from outside the central interior into the central interior, or from within the central interior outside of the central interior.

BRIEF DESCRIPTION OF THE DRAWINGS

The structure, operation, and advantages of the present invention will become further apparent upon consideration of the following description taken in conjunction with the accompanying figures. The figures are intended to be illustrative, not limiting.

Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

Figure 1:
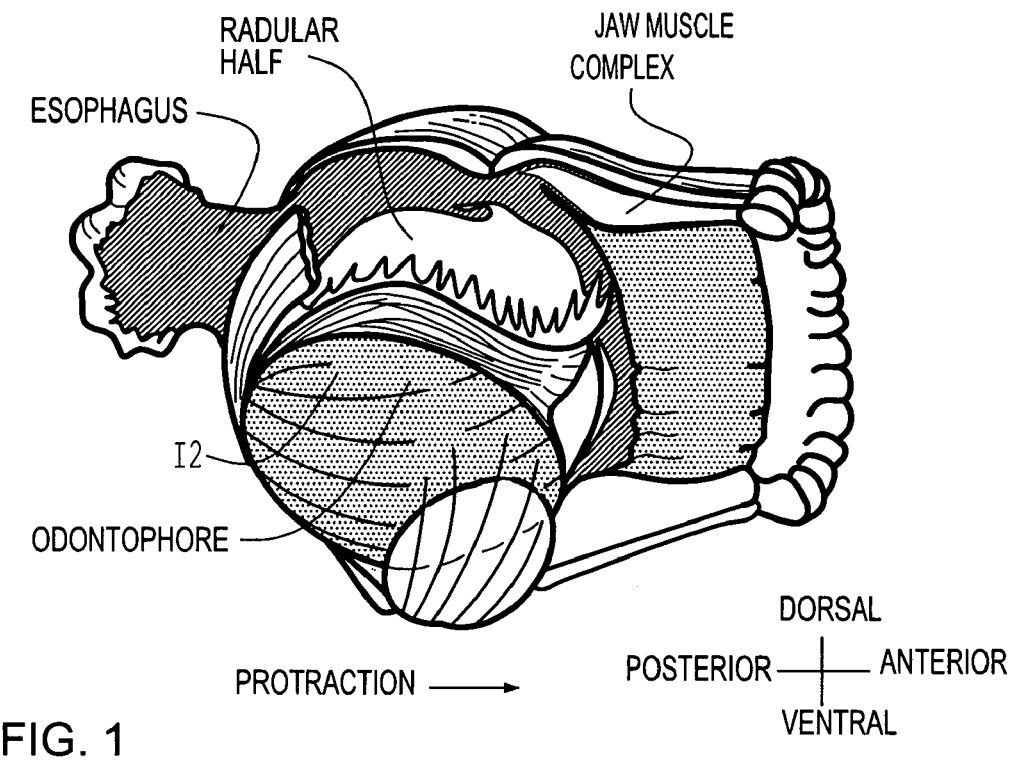

In the drawings accompanying the description that follows, often both reference numerals and legends (labels, text descriptions) may be used to identify elements. If legends are provided, they are intended merely as an aid to the reader, and should not in any way be interpreted as limiting.

Often, similar elements may be referred to by similar numbers in various figures of the drawing, in which case typically the last two significant digits may be the same, the most significant digit being the number of the drawing figure.

FIG. 1 shows a schematic view of the anatomy of the buccal mass of *Aplysia californica;*

Figure 2:
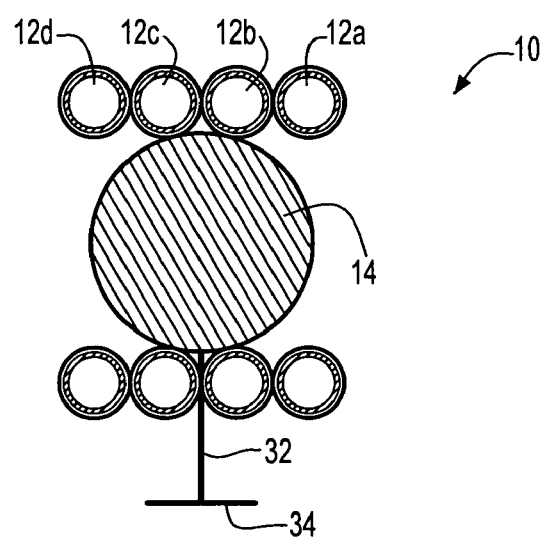

FIG. 2 shows the side view, in cross section, of a flexible gripping device, in accordance with the present invention;

FIGS. 3A-3B are respective side views of an unexpanded and expanded existing art pneumatic actuator;

FIGS. 4A-4B shows the schematic of an inflated and deflated assembly of four pneumatic actuators to form a ring, in accordance with the present invention;

FIGS. 5A and 5B shows the schematic of a first embodiment of a grasper element, in accordance with the present invention;

FIGS. 6A and 6B shows the schematic of a second embodiment of a grasper element, in accordance with the present invention.

Figure 8:
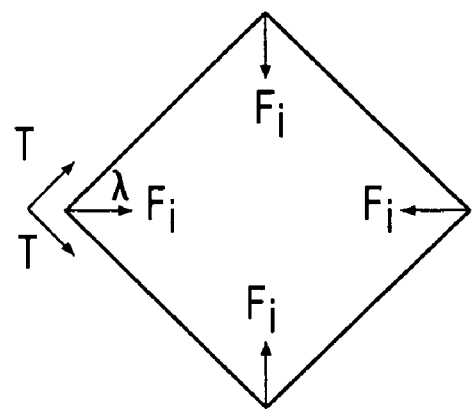
Figure 9:
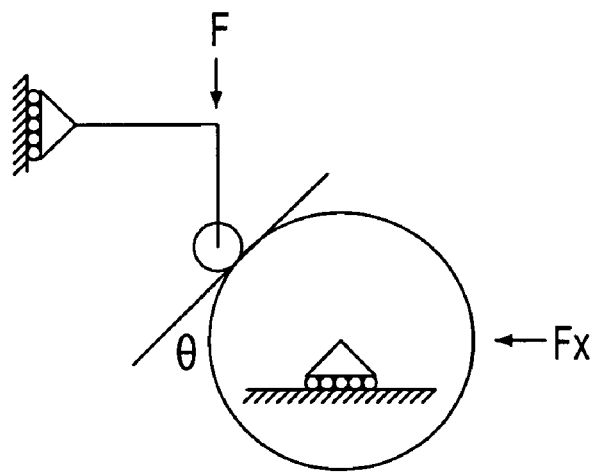

FIGS. 7A and 7B show the operation cycle of the flexible gripping device, in accordance with the present invention;

FIG. 8 shows the force normal to the rings, in accordance with the present invention;

FIG. 9 shows a schematic of the mechanical analysis, in accordance with the present invention;

FIG. 10 shows the free body diagrams for the mechanical analysis of the action of the rings on the central grasper, in accordance with the present invention.

Figure 14:
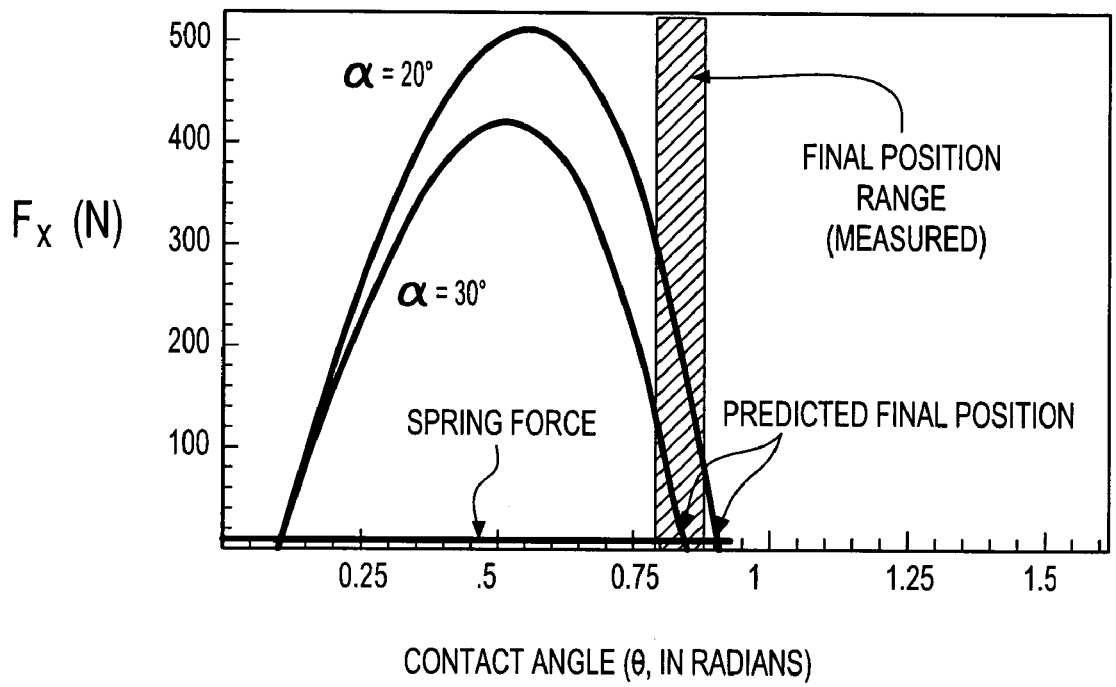
Figure 15:
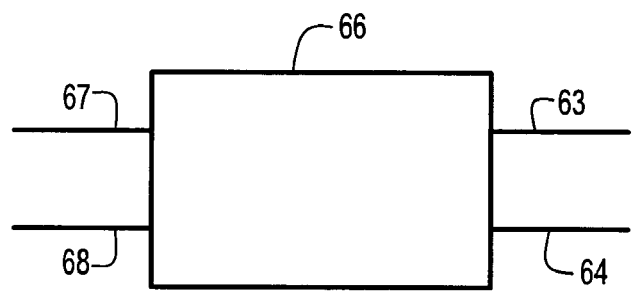

FIG. 11 shows the mechanical analog, in accordance with the present invention;

FIG. 12 shows the schematic of inflatable "lips" type grasper device, in accordance with the present invention;

FIG. 13 shows the schematic of a hinged grasper device, in accordance with the present invention;

FIG. 14 shows predicted and actual positions and a region in which the rings cannot act on the grasper, in accordance with the present invention; and FIG. 15 shows a schematic of a control system, in accordance with the present invention.

DETAILED DESCRIPTION OF THE INVENTION

The present invention relates to a flexible gripping device 10, as shown in FIG. 2, that uses a plurality of braided pneumatic actuators 12a, 12b, 12c, 12d (12a-12d) arranged in rings to form a tube like structure in combination with a grasper element 14. As discussed in more detail below, the flexible gripping device 10 operates to move the grasper element 14 through the lumen or central interior of the tube like structure formed of the plurality of pneumatic actuators (12a-12d). While four rings are shown creating the lumen, it is within the scope of the present invention to use three or more rings depending on the particular application.

The pneumatic actuators (12a-12d), can be modified McKibben artificial muscles that approximate or mimic the function of the I1/I3 jaw muscles of a sea slug as previously described and shown in FIG. 1. A McKibben artificial muscle ring, as shown in FIG. 3A, consists of an expandable bladder 20, such as for example of a latex material, located inside of a tubular mesh 22 made of relatively inextensible fibers, such as for example braided nylon. The mesh 22 is clamped or otherwise affixed to the bladder 20 at its ends 24. As fluid, i.e., gas, air or liquid, is supplied into the bladder 20 through an inlet line 26, the diameter of the bladder 20 expands radially, as shown in FIG. 3B. Because of the inextensible fiber mesh 22, the surface area of the expanding bladder 20 remains relatively constant. Thus, at the time the bladder's diameter increases, its length decreases, i.e., tending from a cylindrical to a more spherical shape, as shown in FIG. 3B. This is understood because the tubular mesh 22 imposes an isovolumetric constraint on the bladder 20, so expansion in the radial direction causes a contraction in the axial direction, as disclosed in Colbrunn, R. W. DESIGN AND CONTROL OF A ROBOTIC LEG WITH BRAIDED PNEUMATIC ACTUATOR, Department of Mechanical and Aerospace Engineering, Case Western Reserve University, 2000. M.S. thesis, p. 1-37.

Referring to FIGS. 4A and 4B, there is illustrated a side view of an actuator ring 30 (corresponding to the ring actuators 12a-12c) in accordance with the present invention. A plurality of pneumatic actuator sections 32a-32d are connected end to end and attached to each other by a cylindrical connector 34 or a t-shaped connector 36. While the actuator ring 30 is shown constructed of four braided, pneumatic actuator sections 32a-32d, it is within the scope of the present invention to use three or more actuator sections depending on the particular application. To actuate the pneumatic actuator sections 32a-32d, pressurized air, gas or liquid of between 2.5 psi and 100 psi and preferably between 10 psi and 60 psi and most preferably between 15 psi and 30 psi is delivered to the interior of the actuator ring 30, of the type shown in FIG. 3A, through an opening such as through the inlet 36a of the t-shaped connector 36. As the outer circumference of the actuator ring 30 is inflated and gets larger, the inner circumference of the actuator ring gets smaller (see FIG. 4B). That is, there is an overall decrease in the diameter d1 of the actuator ring 30 in the uninflated ring in FIG. 4A as compared to the diameter d2 of the inflated actuator ring in FIG. 4B.

The flexible gripping device 10, as generally shown in FIG. 2, includes a grasper element 14 that is initially disposed in the center of the central interior of the tube formed of pneumatic actuator rings 12a-12d, which are disposed in parallel relation to each other. A device 32, such as for example, an elastic band, is provided for returning the grasper element 14 to an initial resting position in the central interior of the tubular device if the actuator rings 12a-12d are not actuated. The elastic band 32 is secured at one end to the grasper element 14. The elastic band 32 extends between rings 12b and 12c and is secured at its opposite end to a substrate 34. The elastic band 32 operates to both constrain the grasper element so that the grasper element rotates and for pulling the grasper element back to the initial resting position. When the device 10 is not anchored, e.g. if it operates autonomously at the end of a moving manipulator, the substrate 34 will move with the end of the manipulator.

Referring to FIGS. 5A and 5B, there is illustrated a first embodiment of the grasper element 40 (corresponding to element 14). The grasper element 40 incorporates a pair of inflatable, lip-like tubular actuators 42 and 44 constructed similar to the braided pneumatic actuators shown in FIG. 3A. The inflatable, lip-like tubular actuators 42 and 44 are disposed around a relatively rigid ellipsoid shaped element 46, such as one formed from rubber. At the approximate center of the ellipsoid 46, there is a groove 47 with a flat bottom surface formed around the circumference of the ellipsoid. The groove 47 is disposed parallel to the minor axis of the generally ellipsoid shaped element. Disposed within the groove 47 are a pair of tubular actuators 42 and 44 that are placed against the edge walls 47a and 47b of groove 47 and held in place by any desired means such as a rubber band 48 secured to opposite ends of the actuators or artificial muscles 42 and 44. The actuators 42 and 44 extend around the circumference of the groove 47 for about 5° to about 345° and preferably about 60° to about 180° and most preferably about 90° to about 180°. Each of the actuators 42 and 44 has an air, gas or liquid line 49 for inflating the inflatable lip-like tubular actuators 42 and 44. When the actuators 42 and 44 are inflated by air or any other inflation fluid, they expand radially press against each other, as shown in FIG. 5B so as to be able to squeeze on a material to be moved. At the same time, the length of the actuators 42 and 44 decreases as shown in FIG. 5B and as previously described.

A second embodiment of a hinged grasper element 50 (corresponding to element 14) is shown in FIGS. 6A and 6B. The hinged grasper element 50 is constructed of a generally spherically shaped, flexible element 51, such as an elastomeric or rubber ball. The spherically shaped element 51 has a cleft opening 52 formed therein. The cleft opening 52 typically has a generally wedge like shape that extends from the peripheral surface 54 of the spherically shaped element 51 to a location near a centerline 55 extending through the spherically shaped element. The angle "a" of the wedge shaped opening 52 is preferably between about 5° to about 45° and preferably about 15° to about 40° and most preferably about 25° to about 35°. On the opposite side of the spherically shaped element 51 from the wedge shaped opening 52 is formed a second cleft opening 56, generally of a wedge like shaped which can be substantially identical to the cleft opening 52. There is a small section of flexible material separating the cleft openings 52 and 56 and providing a hinge-like action between the two openings. It is within the terms of the invention to form the second opening 56 with a different shape than first opening 52, depending on the particular design and application for which the grasper element will be used. Within the cleft opening 56 is a means 58 to provide a passive closing force. The means can be a torsional spring hinge secured to the wedge walls 56a and 56b. One or more pneumatic actuators or artificial muscles 60 (operating by the principles described before see FIG. 3A) are attached at opposite ends to the peripheral surface 54 of the spherically shaped element 51 and extend across the opening 56. Each of the actuators or artificial muscles 60 can be disposed in a groove 54a as shown in FIG. 6B. When activated (see FIG. 6A), the artificial muscle(s) 60 contract and shorten (according to the principles previously described) to close the cleft opening 56 against the bias force of spring 58. Simultaneously, the cleft opening 52 is opened as shown in FIG. 6A. Then, when the artificial muscle(s) 60 are expanded by relieving the pressure in the artificial muscle(s) 60, the bias force of spring 58 opens cleft opening 56 (see FIG. 6B) and simultaneously causes the cleft opening 52 to close. When cleft opening 52 closes, it is capable of grasping some object in accordance with the present invention.

A peristaltic cycle is used to control the gripper device 10 as generally shown in FIGS. 7A and 7B. Using compressed air at a desired pressure, e.g., 60-75 psi, each of the rings 12a-12d can be alternately contracted and then expanded. The elastic band 32 kinematically induces the grasper element 14 to rotate as it is protracted (see FIG. 7A), and pulls the grasper element 14 back to its initial resting position once the rings 12a-12d are deflated.

With the grasper element 40, of the type shown in FIGS. 5A and 5B, at the start of a protraction, i.e., the rest position as shown in FIG. 7A, the inflatable, lip like actuators 42 and 44 are open as shown in FIG. 5A. Then ring 12c is activated to start the grasper element's movement to the peak protraction location. Next, ring 12b and finally ring 12c are activated so that the grasper element moves to the peak protraction location. Once peak protraction is reached, the inflatable lip like actuators close (see FIG. 5B) on a material to be grasped. Then rings 12a-12c are relaxed, by lowering the pressure on the actuating gas or fluid and the grasper element 40 is passively pulled back to its rest position by the elastic band 32. As shown in FIG. 7A, ring 12c can be relaxed prior to relaxing rings 12a and 12b.

Next, as shown in FIG. 7B, the grasper element 40 is actively retracted by the rings, while the lip like actuators remain in the closed position (see FIG. 5B), until peak retraction is reached. First ring 12b is activated to start the grasper element's movement to the peak retraction location. Next ring 12c and finally ring 12d are activated so that the grasper element moves to the peak retraction location. The inflatable lip like actuators 42 and 44 then open again (see FIG. 5A) and can deposit the grasped material on the outward side of ring 12d and opposite from the side of the gripper device 10 from where it was initially grasped. Next, by lowering the pressure on the actuating gas or fluid on the rings 12b, 12c and 12d, the grasper element 14 is passively pulled back to the rest position by the elastic band 32 while the inflatable lip like actuators 42 and 44 remain in the open position so that the cycle can repeat. As shown in FIG. 7B, ring 12b can be relaxed prior to relaxing rings 12c and 12d.

In another embodiment, the gripper device 10 can operate the same way as just described but the hinged grasper element 50 can be substituted for the grasper element 40. When the grasper element 50, as shown in FIGS. 6A and 6B, is in the rest position at the start of a protraction as shown in FIG. 7A, the cleft opening 52 is open as shown in FIG. 6A. Once peak protraction is reached, the cleft opening 52 is closed (see FIG. 6B) on the material to be grasped. Then rings 12a-12c relax and the grasper element 50 is passively pulled back to its rest position by the elastic band. Next, as shown in FIG. 7B, the grasper element 50 is actively retracted while remaining in the closed position (see FIG. 5B) by the rings until peak retraction is reached. The cleft opening 52 is then opened again (see FIG. 6A) and the grasped material is deposited on the other side of the rings from which it was initially grasped. Next, the grasper element 50 while in the open position is passively pulled back to the rest position, as previously described, and the cycle can repeat.

The sequence of operations described here can be reversed, so that the grasper (embodied either as 40 or 50 or in a functionally equivalent form) can close upon material within the lumen while the grasper is retracted, and then the grasper can be protracted, and the material can be released outside of the lumen. Thus, the device could be used for transport of material in either direction through the lumen.

It is possible to compute the force that a ring will exert on a grasper element. If the ring contacts the grasper at four points, the force produced by the axial contraction of the artificial muscles can be translated to a force normal to the rings (See FIG. 8).

The force at each contact point i is $2\,T\cos\lambda$. Since the ring actually contacts the grasper at m points, the total force F over m contact points is $2\,T\cos\lambda$. $2Tm\cos\lambda$. The angle $\lambda$ is $\pi/2-\pi/m$, and so the force, F, becomes $2\,T\,m\,\cos(\pi/2-\pi/\mu)$, which is equal to $2Tm\sin\pi/m$. As m increases to infinity, as it does for a circular ring, the value of $\sin\pi/m$ approaches $\pi/m$ and so the total inward force around the ring becomes $$F = 2Tm\frac{\pi}{m} = 2\pi T. \tag{1}$$

To compute the force on the gripper in the horizontal direction, we analyze the device as shown in FIG. 9. We assume that the rings can only move vertically (constraint force F), and the grasper can only move horizontally (constraint force Fx). This is mechanically equivalent to the diagram shown in FIG. 11.

The relationship between the input force, F, and the net horizontal force, Fx, can now be determined from a free body diagram (see FIG. 10). Using the free body diagram for the ring, which includes the normal force, N, on the grasper (see FIG. 10A), the frictional force, µN, and the force, F, generated by the actuators, the sum of the forces in the y direction is $F-N\cos(\theta)-\mu N\sin(\theta)$. Thus the normal force N is equal to $$N = \frac{f}{\cos\theta + \mu\sin\theta}. \tag{2}$$

From the free body diagram of the grasper, the horizontal components of the normal and frictional forces sum to $N\sin(\theta)-\mu N\cos(\theta)-Fx$. Substituting (2) into this equation yields $$\frac{F\sin\theta}{\cos\theta + \mu\sin\theta} - \frac{\mu F\cos\theta}{\cos\theta + \mu\sin\theta} - F_x = 0 \tag{3}$$

which simplifies to $$\frac{F_x}{F} = \frac{\sin\theta - \mu\cos\theta}{\cos\theta + \mu\sin\theta} \quad (4)$$

Plotting equation (4) shows that at low angles of contact, friction creates a dead zone in which no application of force will cause the grasper to move forward (see FIG. 14, left side). Since F=2πT, the overall force of the ring on the grasper becomes $$F_x = 2\pi T \frac{\sin\theta - \mu\cos\theta}{\cos\theta + \mu\sin\theta}. \quad (5)$$

Finally, to convert the pressure in the McKibben actuator into tension T, we use a model of the forces within the actuator [Colbrunn, 2000]:

$$T = \frac{b^2 P (3L^2/b^2 - 1)}{4\pi n^2} \quad (6)$$

where L is the current length of the actuator, n is the number of helices in the actuator, b is the length of a strand of braid which is estimated from the braid angle α[the greek letter alpha] using the equation b=L/cos α[the greek letter alpha], and P is the input pressure of the actuator.

In an actual test, the inflatable lip like actuator 40 was able to protract, grab a piece of silicon tubing, then retract and deposit the tubing on the other side of the rings (see FIG. 12). During operation, the grasper 40 could do this repeatedly with a cycle time of 16 seconds.

In another actual test, the hinged grasper 50 was able to protract, grasp a piece of silicon tubing, retract, and then deposit the tubing on the other side of the rings (See FIG. 13).

At this stage of development, the maximum amount of force that the rings imposed on the inflatable "lips" gripper is estimated by measuring the restoring force in the elastic hinge, which is equal and opposite to the force exerted by the gripper when the hinged grasper 50 was fully protracted or fully retracted. In one test, the force was approximately 5 newtons (N).

Based on the theoretical analysis done above, and measurements from the grasper devices, it is possible to calculate the force that the rings should optimally exert on the grasper. The number of helices (n) in an actuator segment was 1, the length of a strand of a braid (b) was 7.4 cm, the input pressure (P) was 60 psi, equal to 410 kPa, and the length (L) of the actuator was 7 cm. Using equations (5) and (6), and the measured spring force, the final extended position of the grasper when the most anterior ring was fully actuated could be estimated. The predicted position matched the actual position very well (see FIG. 14).

By adding physical property sensors, such as pressure sensors 60, 61, or other sensors (e.g., temperature, chemical) to the inner surfaces 47 of the grasper device 40 or inner surface of cleft opening 52 of the grasper device 50, respectively, (see FIGS. 5B and 6A) or to an inner surface of a functionally equivalent embodiment of a grasper device), the flexible gripping device 10 could sense the physical properties or local conditions encountered by the grasper element as it grasped material, and could flexibly and rapidly respond to these changes in conditions. Pressure sensors 60, 61 can be connected by lines 63 and 64 to a control system 66 such as a computer or a neural network that controls the braided pneumatic actuators 12a-12d by one or more lines 67 and actuators 42 and 44 of grasper 40 and/or the actuators or artificial muscles 60 of grasper 50 by one or more control lines 68. That is, the control system 66 could respond to changes in physical properties encountered by the grasper element by altering the duration or intensity of protraction or retraction of the grasper element through the flexible gripping device 10 or opening or closing of the grasper element. In addition, the control system could change the timing of opening and closing the grasper element relative to protraction and retraction of the plurality of actuator rings so that material can be transported from outside the central interior (lumen) into the central interior, or from within the central interior outside of the central interior of the tubular shaped flexible gripping device 10. For example, if the grasper failed to encounter material, it could protract further, rather than performing a full protraction/retraction cycle. If the material resisted attempts to pull it into the lumen of the flexible gripping device, the flexible gripping device could sense this and increase the force (intensity) it exerted.

The present application describes a biologically-inspired gripping device 10 that can transfer pliable materials through a lumen. The gripping device 10 has many potential applications including surgically removing plaque from blood vessels and cleaning plumbing to name a few.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described inventive components the terms are intended to correspond, unless otherwise indicated (sensing, controlling, exerting force, etc.) the terms (including a reference to a "means") used to describe such components are intended to correspond, unless otherwise indicated, to any component that performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A flexible gripping device comprising:
    a plurality of pneumatic actuator rings;
    a grasper element disposed within the plurality of pneumatic actuator rings and adapted to move back and forth within the actuator rings;
    means for sequentially activating the plurality of actuator rings to produce a peristaltic motion that moves the grasper element back and forth within the actuator rings, wherein the plurality of actuator rings are disposed in parallel relation to each other and are secured to each other to form a tubular device with a central interior through which the grasper element moves back and forth;
    means to actuate the actuator rings to move the grasper element forwards or backwards relative to the central interior of the tubular device; and means for returning the grasper element to an initial resting position in the central interior of the tubular device if the actuator rings are not actuated.

2. The gripping device of claim 1, including:
means of connecting each of the actuator rings to an adjacent ring so that each of the actuator rings remain in contact with adjacent rings as any ring expands or contracts whereby each ring may expand in volume and occupy part of the central interior so as to exert force on the grasper element.

3. The gripping device of claim 1 wherein the means for returning the grasper element is an elastic band attached to the grasper element and to a substrate for constraining the grasper element to rotate and for pulling the grasper element back to the initial resting position.

4. The flexible gripping device of claim 1, further including:
means of sensing at least one physical property encountered by the grasper element; and
means of controlling the gripping device in response to the at least one physical property encountered by the grasper element.

5. The flexible gripping device of claim 4, wherein the means of controlling the gripping device further includes:
means for responding to changes in the at least one physical property encountered by the grasper element by altering the duration or intensity of protraction or retraction of the grasper element or opening or closing of the grasper element.

6. The flexible gripping device of claim 4, wherein the means of sensing the at least one physical property includes at least one of a pressure sensor, a temperature sensor, and a chemical sensor.

7. The flexible gripping device of claim 1, wherein the pneumatic actuator ring includes a plurality of actuator sections.

8. A flexible gripping device comprising:
a plurality of pneumatic actuator rings; and
a grasper element disposed within the plurality of pneumatic actuator rings and adapted to move back and forth within the actuator rings;
wherein the grasper element comprises:
a generally spherically shaped, elastomeric element;
a first cleft shaped opening extending from a peripheral surface towards the interior of the elastomeric element;
a second cleft shaped opening extending from an opposite side of the peripheral surface towards the interior of the elastomeric element;
means within the second cleft shaped opening to provide a passive closing force; and
at least one pneumatic actuator disposed across the second cleft shaped opening and attached at opposite ends of the actuator to the peripheral surface for opening the second cleft shaped opening and simultaneously closing the first cleft shaped opening so as to enable them to grasp a material to be moved.

9. The gripping device of claim 8, wherein the means to provide a passive closing force is a spring.

10. The gripping device of claim 8, wherein:
the first cleft shaped opening is a generally wedge shaped opening of an angle of between about 5° to about 45'; and
the second cleft shaped opening is a generally wedge shaped opening that is substantially identical to the first generally wedge shaped opening.

11. A flexible gripping device comprising:
a plurality of pneumatic actuator rings; and
a grasper element disposed within the plurality of pneumatic actuator rings and adapted to move back and forth within the actuator rings;
wherein the grasper element comprises:
a generally ellipsoid shaped element with a groove having a flat bottom surface formed around the circumference of the ellipsoid shaped element;
a pair of inflatable tubular actuators disposed in the groove and spaced from each other;
means to inflate the tubular actuators so that they expand radially and press against each other to enable a material to be grasped and moved.

12. The gripping device of claim 11, wherein the grasper element includes means for securing the pair of inflatable tubular actuators disposed in the groove.

13. The gripping device of claim 11, wherein the groove in the grasper element is disposed parallel to the minor axis of the generally ellipsoid shaped element.

14. The gripping device of claim 11, further including:
means of returning the grasper element to an initial resting position if the actuator rings are not actuated.

* * * * *